US009585661B2

(12) United States Patent
Deperne et al.

(10) Patent No.: US 9,585,661 B2
(45) Date of Patent: Mar. 7, 2017

(54) SURGICAL CLIP APPLIER

(71) Applicant: Peters Surgical, Bobigny (FR)

(72) Inventors: Denis Deperne, Vern sur Seiche (FR); Adrien Fiorino, Rennes (FR)

(73) Assignee: PETERS SURGICAL, Bobigny (FR)

(*) Notice: Subject to any disclaimer, the term of this patent is extended or adjusted under 35 U.S.C. 154(b) by 0 days.

(21) Appl. No.: 15/053,556

(22) Filed: Feb. 25, 2016

(65) Prior Publication Data

US 2016/0249925 A1 Sep. 1, 2016

(30) Foreign Application Priority Data

Feb. 26, 2015 (EP) .................................. 15305297

(51) Int. Cl.
*A61B 17/10* (2006.01)
*A61B 17/128* (2006.01)
*A61B 17/00* (2006.01)

(52) U.S. Cl.
CPC ............ *A61B 17/10* (2013.01); *A61B 17/128* (2013.01); *A61B 2017/00473* (2013.01); *A61B 2090/035* (2016.02)

(58) Field of Classification Search
CPC . A61B 17/10; A61B 17/128; A61B 2090/035; A61B 2017/00473
See application file for complete search history.

(56) References Cited

U.S. PATENT DOCUMENTS

| 4,187,712 A * | 2/1980 | Samuels ............ A61B 17/122 72/409.01 |
| 4,681,107 A | 7/1987 | Kees, Jr. |
| 5,735,857 A * | 4/1998 | Lane .................. A61B 17/8872 606/207 |
| 5,925,052 A | 7/1999 | Simmons |
| 2003/0028216 A1* | 2/2003 | Hanson ............. A61B 17/2812 606/205 |
| 2004/0093020 A1* | 5/2004 | Sinton ................ A61B 17/2816 606/208 |

(Continued)

FOREIGN PATENT DOCUMENTS

| EP | 0116220 | 8/1984 |
| FR | 452248 | 5/1913 |

(Continued)

OTHER PUBLICATIONS

European Search Report for European Application No. 15305297, (Oct. 26, 2015).

*Primary Examiner* — Richard Louis
(74) *Attorney, Agent, or Firm* — Blakely Sokoloff Taylor & Zafman LLP

(57) ABSTRACT

A surgical clip applier comprises a first arm (12) and a second arm (14) pivotable relative to each other and defining proximal ends (16, 18) for manually controlling the applier, and distal ends (26, 28); jaws (30) positioned between the distal ends such (26, 28) that pivot of the first arm (12) relative to the second arm (14) opens and closes the jaws (30); and a setting element (32) movably mounted in one (12) of the first arm and the second arm and extending into contact with the other (14) of the first arm and the second arm to define a maximum open position of the first arm (12) relative to the second arm (14), and wherein a change of position of the setting element (32) adjusts the maximum open position.

13 Claims, 13 Drawing Sheets

(56) References Cited

U.S. PATENT DOCUMENTS

2006/0161182 A1* 7/2006 Vandenbroek ....... A61B 17/128
　　　　　　　　　　　　　　　　　　　　606/142
2007/0073314 A1　3/2007　Gadberry

FOREIGN PATENT DOCUMENTS

| WO | WO-0228268 | 4/2002 |
| WO | WO-2005099592 | 10/2005 |

* cited by examiner

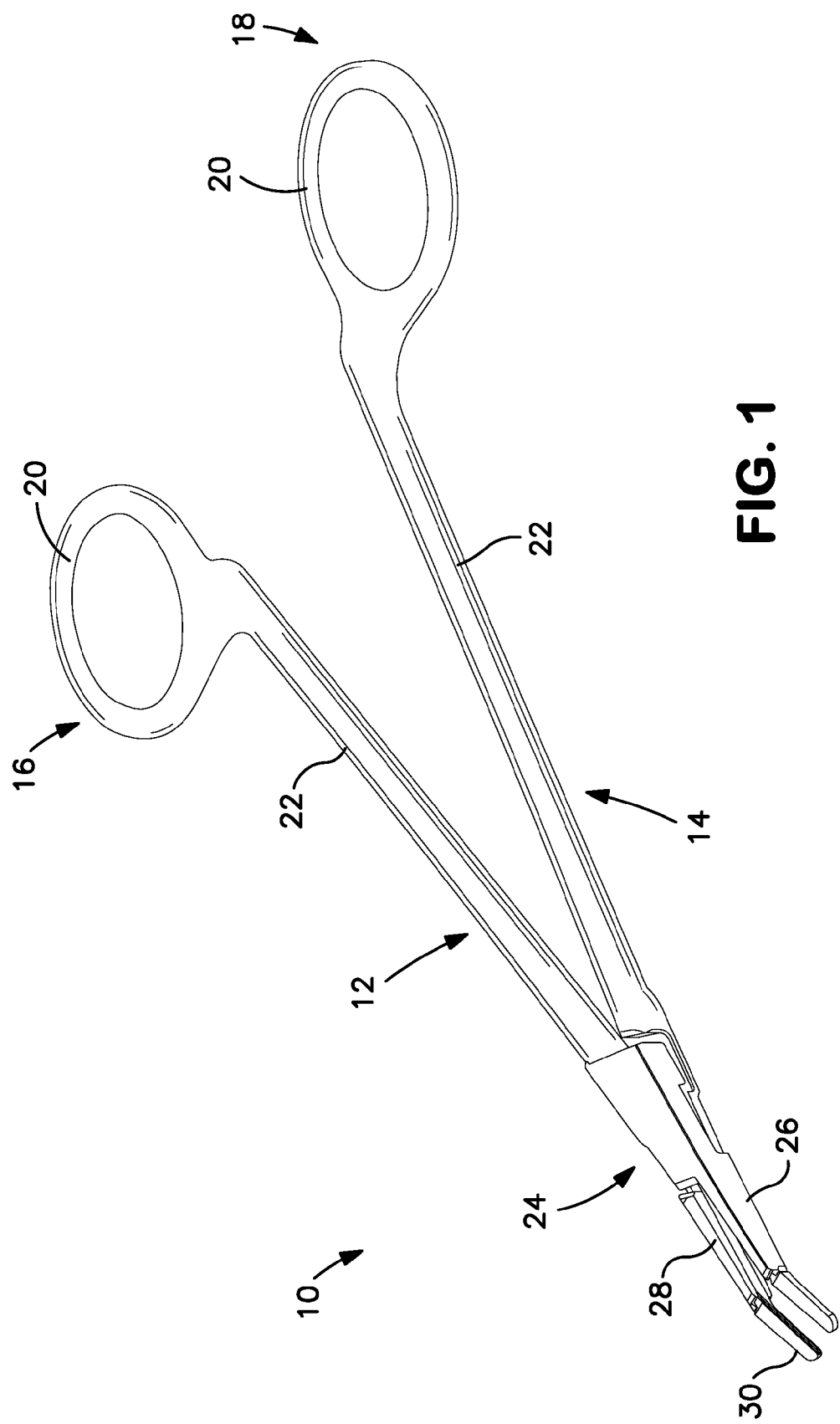

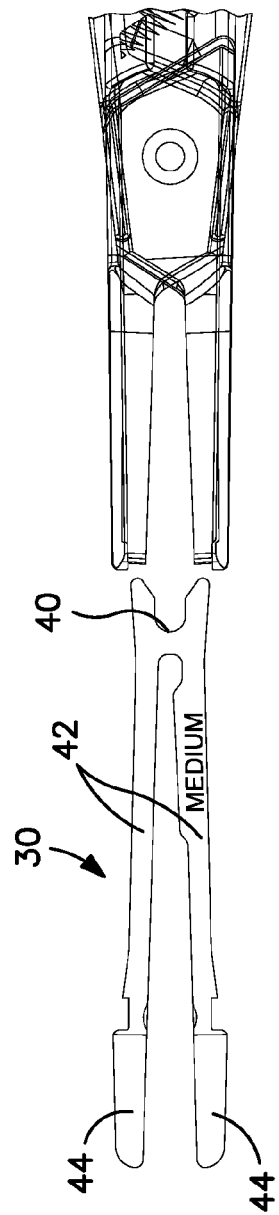
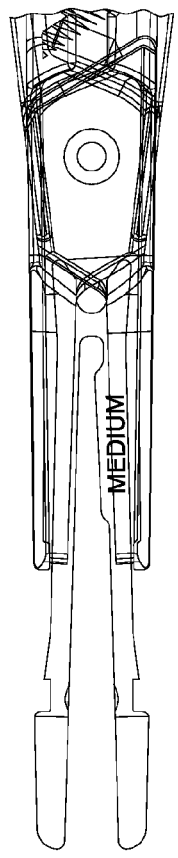
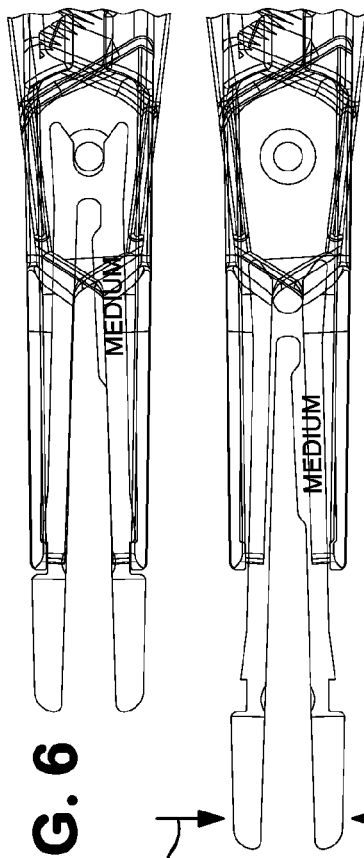
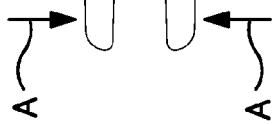
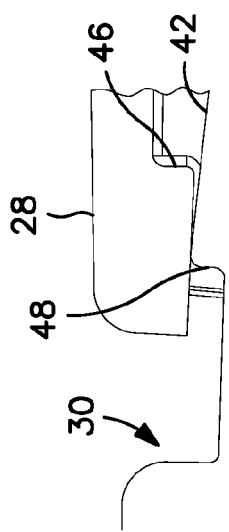
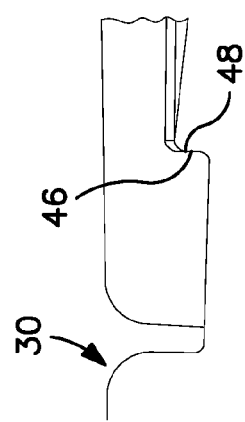
FIG. 4
FIG. 5
FIG. 6
FIG. 7
FIG. 8
FIG. 9

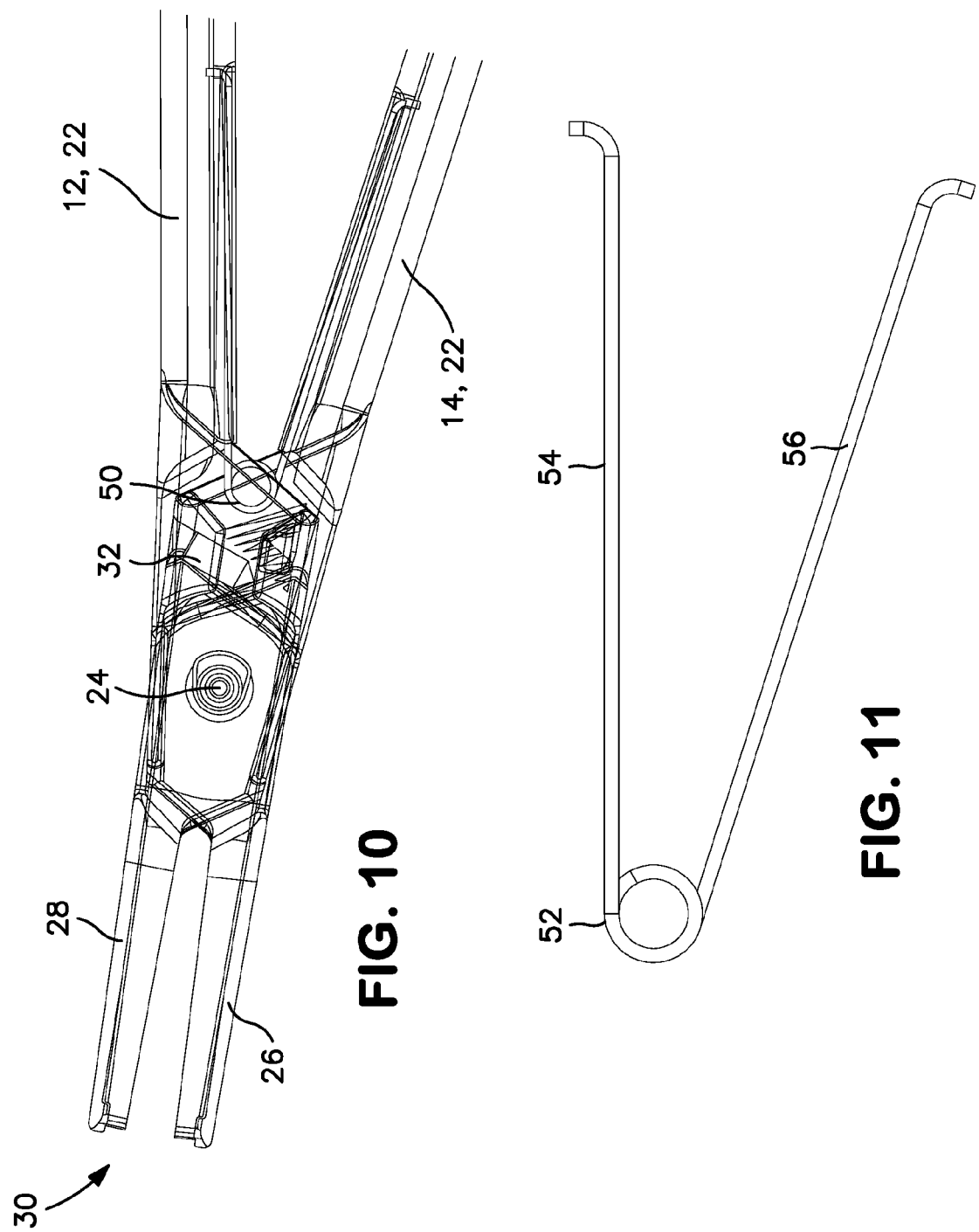

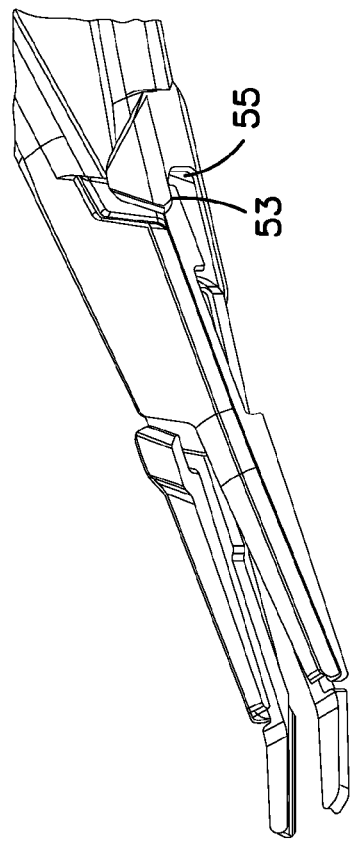
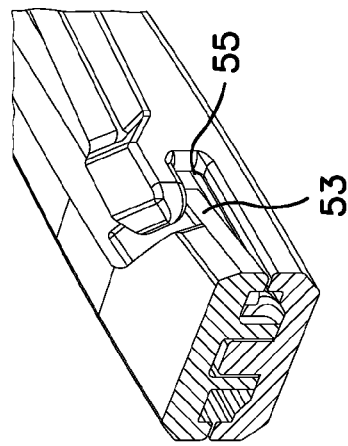
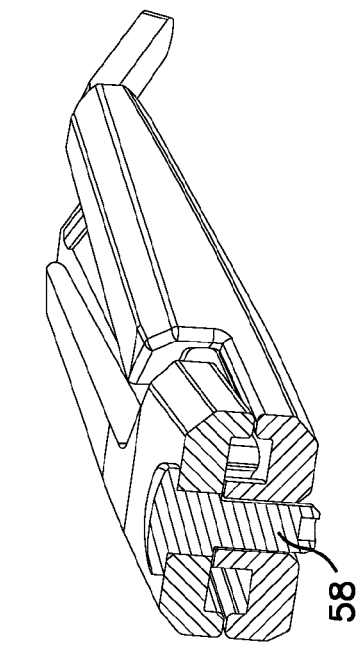
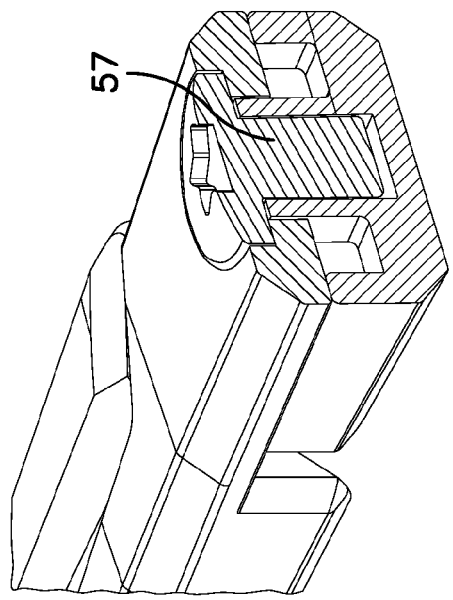
FIG. 13
FIG. 14
FIG. 15
FIG. 16

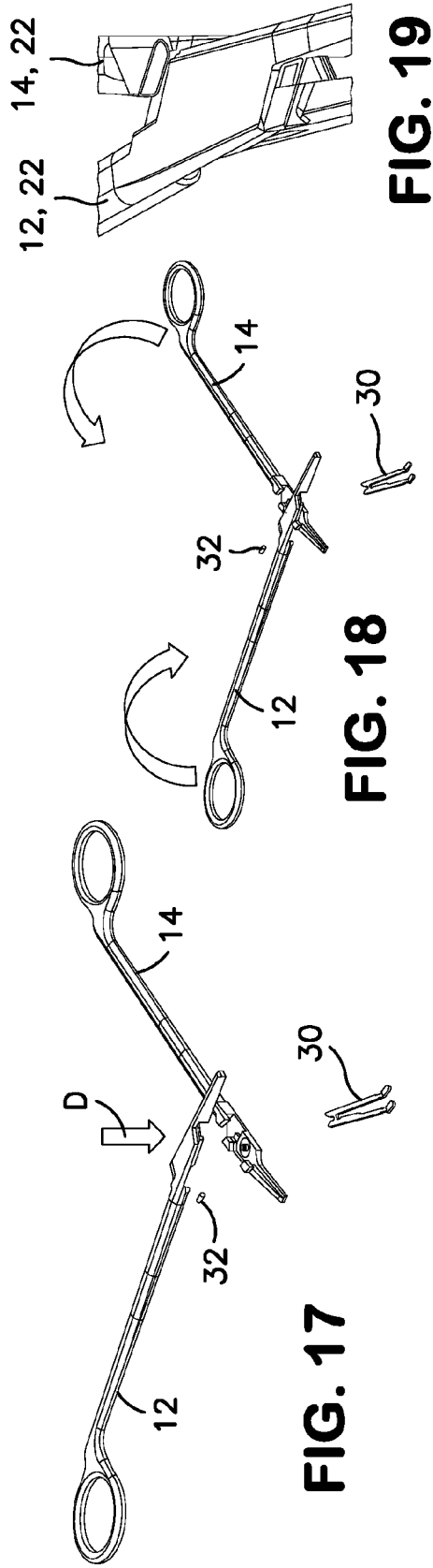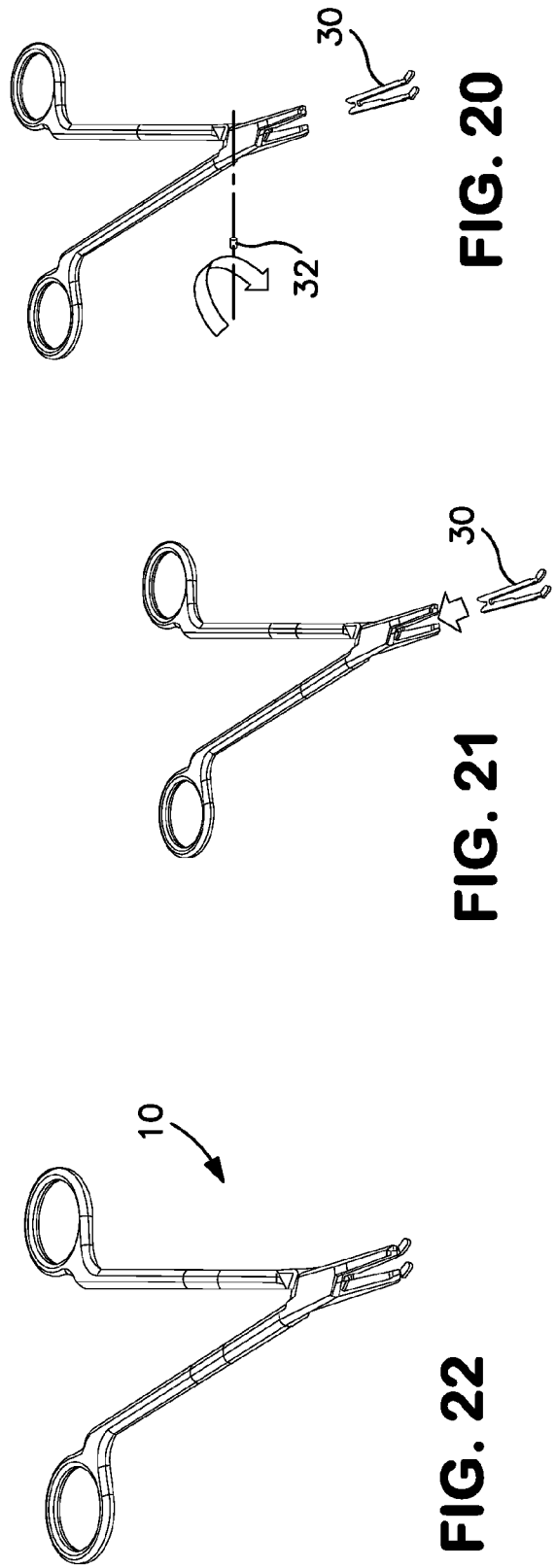

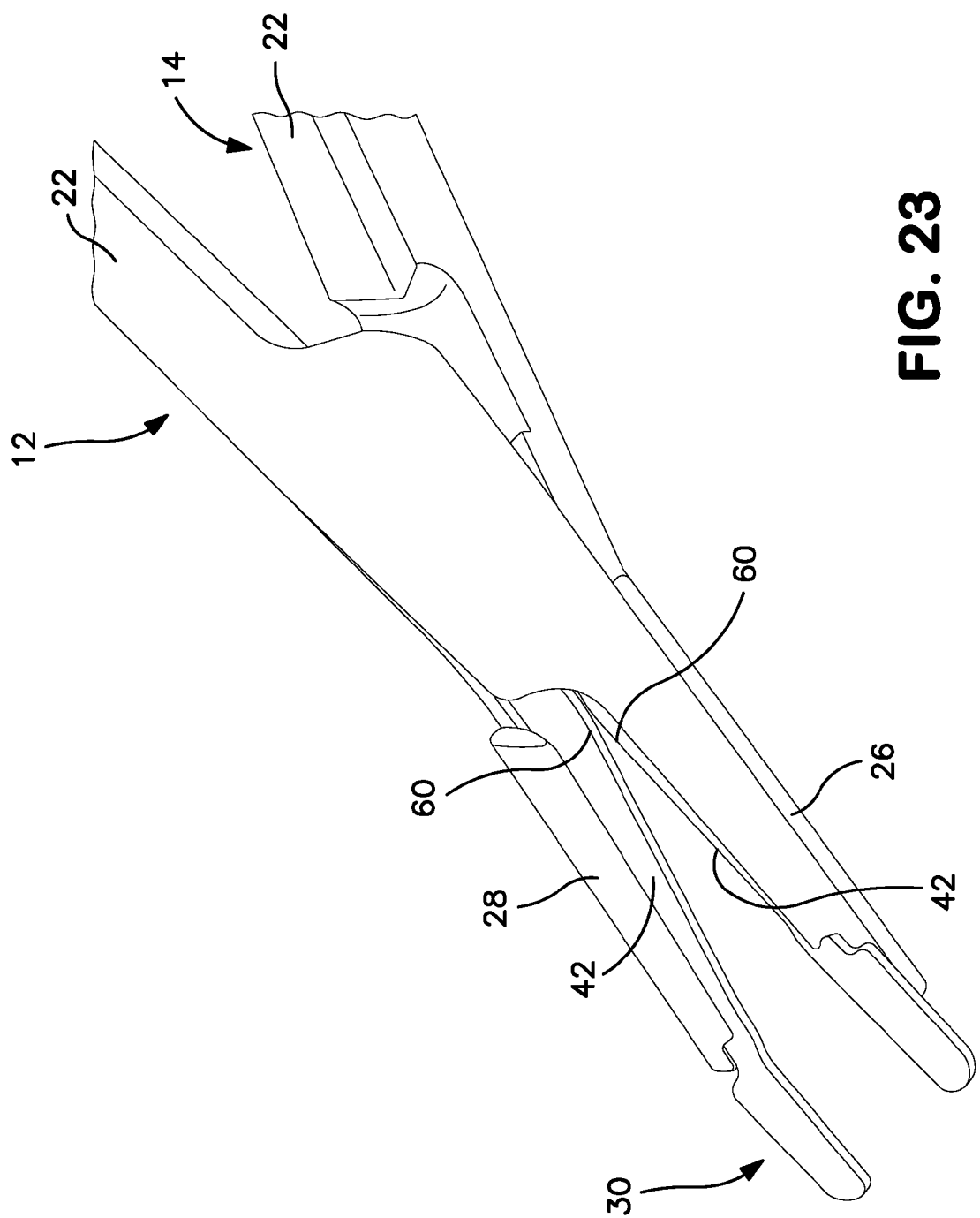

SURGICAL CLIP APPLIER

BACKGROUND OF THE INVENTION

The invention relates to a surgical clip applier.

Surgical clip appliers are used to apply surgical clips or fasteners to tissues and other areas of a surgical site during the course of various surgical procedures. Clip appliers include automatic and manual appliers, and the present invention is directed toward manual appliers.

Known clip appliers include jaws which are used to hold a clip and a mechanism which is used to close the jaws so that the clip can be closed upon the desired location. These devices must be precise, reliable and user friendly for the surgeon. Producing these qualities, however, frequently requires the applier to be complicated and expensive, which is not conducive to a single-use item. In addition, the complex structures incorporated into such apparatus are problematic during cleaning and sterilization.

Another issue with known clip appliers is over-opening of the jaws. This is problematic because if jaws open too far, a clip held in the jaws can inadvertently be dropped, potentially within the surgical site with obvious complications resulting therefrom.

The focus of the present invention is to overcome the above-identified disadvantages.

SUMMARY OF THE INVENTION

In accordance with the invention, the foregoing issues are addressed. As disclosed herein, a surgical clip applier is provided which has a setting screw advantageously positioned to allow precise setting of a maximum open width of the jaws. Further, the clip applier of the present invention can have jaws which are easily installed and removed from the body of the clip applier, thus making the jaws reposable and allowing for extended use of the components of the arms or handle portion of the applier.

According to the invention, a surgical clip applier is provided which comprises a first arm and a second arm pivotable relative to each other and defining proximal ends for manually controlling the applier, and distal ends; jaws positioned between the distal ends such that pivot of the first arm relative to the second arm opens and closes the jaws; and a setting element movably mounted in one of the first arm and the second arm and extending into contact with the other of the first arm and the second arm to define a maximum open position of the first arm relative to the second arm, and wherein a change of position of the setting element adjusts the maximum open position.

The surgical clip applier may further comprise the following features, taken alone or in combination whenever it is technically possible.

The setting element may be a setting screw threadedly mounted in one of the first arm and the second arm and extending into contact with the other of the first arm and the second arm to define a maximum open position of the first arm relative to the second arm, and wherein rotation of the setting screw changes a position of the setting screw and thereby adjusts the maximum open position.

The first arm and the second arm may each define portions which are proximal of a pivot point between the first arm and the second arm such that the portions move toward each other during opening of the arms, wherein the setting element extends from the portion of the first arm toward the portion of the second arm.

The jaws may be releasably held between the distal ends.

The jaws may have a proximal groove sized to fit around a pivot between the first arm and the second arm, and a snap structure defined between the jaws and the distal ends to releasably hold the jaws between the proximal ends.

When the jaws are engaged with the distal ends for use of the applier, the groove may engage the pivot and the snap structure may be engaged.

The jaws may be configured such that squeezing the jaws toward each other disengages the snap structure.

The surgical clip applier may comprise at least one biasing member for resiliently biasing the jaws toward an open position.

The biasing member may comprise a first prong positioned along the first arm and a second prong positioned along the second arm to apply an opening force to the first arm and the second arm, wherein the prongs are parts of the jaws.

At least one of the prongs may have a knee for biaising the prong toward a bent configuration whenever the prong is straightened, the knee being further arranged to come into contact with the other prong then straighten the bent prong whenever the jaws are moved towards each other.

The biasing member may comprise an opening spring positioned relative to the first arm and the second arm to apply an opening force to the first arm and the second arm.

The first arm may be pivotably mounted to the second arm with at least one slidable plate on one arm engaged in a groove on the other arm.

The first arm may be pivotally mounted to the second arm with a screw assembly.

the first arm may be pivotably mounted to the second arm with a tapped rivet.

According to the invention, a method for assembling a surgical clip applier is provided which comprises the steps of: engaging a first arm with a second arm along curved surfaces defining a pivot point between the first arm and the second arm; pivoting the first arm toward the second arm to engage the curved surfaces of the pivot point against separation from each other; adjusting a setting element in one arm relative to the other arm to set a maximum open position of the first arm relative to the second arm; and inserting a jaws member into engagement with distal ends of the first arm and the second arm, whereby the clip applier is assembled and ready for use.

Other objects, advantages and details of the present invention will be further discussed hereinbelow.

BRIEF DESCRIPTION OF THE DRAWINGS

A detailed description of preferred embodiments of the invention follows, with reference to the attached drawings, wherein:

FIGS. 1 and 1A are perspective illustrations of a surgical clip applier in accordance with the present invention;

FIGS. 4-7 illustrate installation and removal of jaws from a surgical clip applier in accordance with the present invention;

FIGS. 8 and 9 illustrate the snap in structure which hold jaws in the surgical clip applier in accordance with the present invention;

FIGS. 10 and 11 illustrate an additional opening spring which may be included in certain embodiments of the present invention;

FIGS. 13 and 14 illustrate one embodiment of the structure of the pivot connection of a surgical clip applier in accordance with the present invention;

FIGS. 15 and 16 illustrate alternate pivot connections;

FIGS. 17-22 illustrate a method for assembling a surgical clip applier in accordance with the present invention; and FIGS. 23 and 23A illustrate another embodiment of the invention.

DETAILED DESCRIPTION

The invention relates to a surgical clip applier which has enhanced adjustability to a maximum open position, reposable jaws and improved simplicity from an assembly, use, and sterilization standpoint.

Figure 1A:
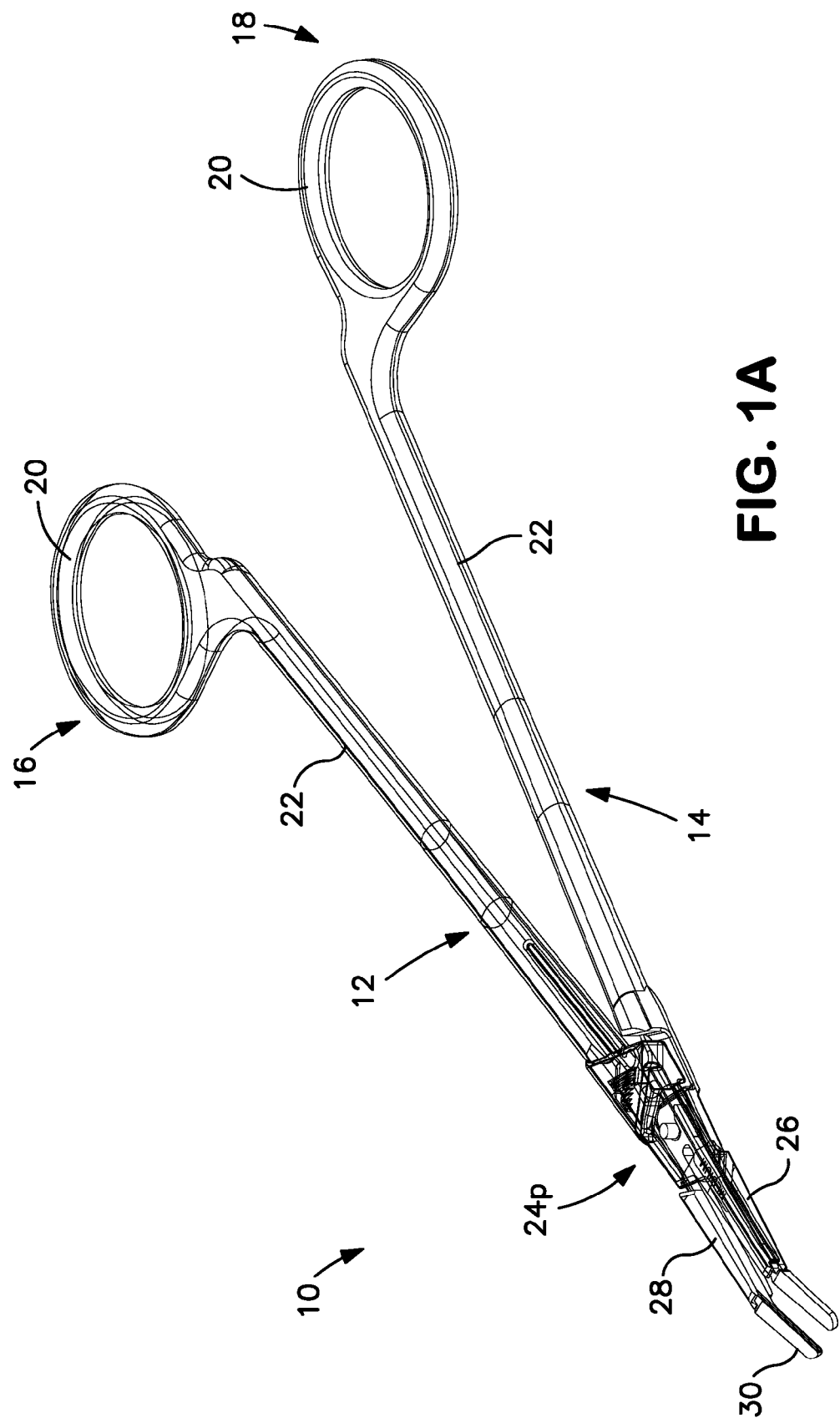

FIGS. 1 and 1A show a surgical clip applier 10 in accordance with the present invention, wherein FIG. 1A shows some components of FIG. 1 transparently to illustrate inner details. Applier 10 has a first arm 12 and a second arm 14, which are pivotally connected with each other to form a scissor-like instrument. Proximal portions 16, 18 of arms 12, 14 can be formed as loops 20 or other suitable structures to facilitate the manual operation of the applier, for example by being gripped in one hand of a surgeon.

Shaft portions 22 lead from proximal portions 16, toward a pivot point 24 and distal portions 26, 28 extend from pivot point 24.

Jaws 30 are positioned between distal portions 26, 28 such that operation of arms 12, 14 to pivot around pivot point 24 serves to open and close distal portions 26, 28 and jaws 30 positioned therebetween.

As is well known to persons skilled in this art, jaws 30 are used to manually apply surgical clips, one at a time, to desired locations or tissues within a surgical site. Arms 12, 14 define a scissor-like instrument which is manipulated by the surgeon or other person using the clip applier to open and close the jaws 30 such that a clip disposed between the jaws can be closed onto a desired location. After application of a clip, the jaws are opened and a new clip is positioned in the jaws for the next application.

Figure 2:
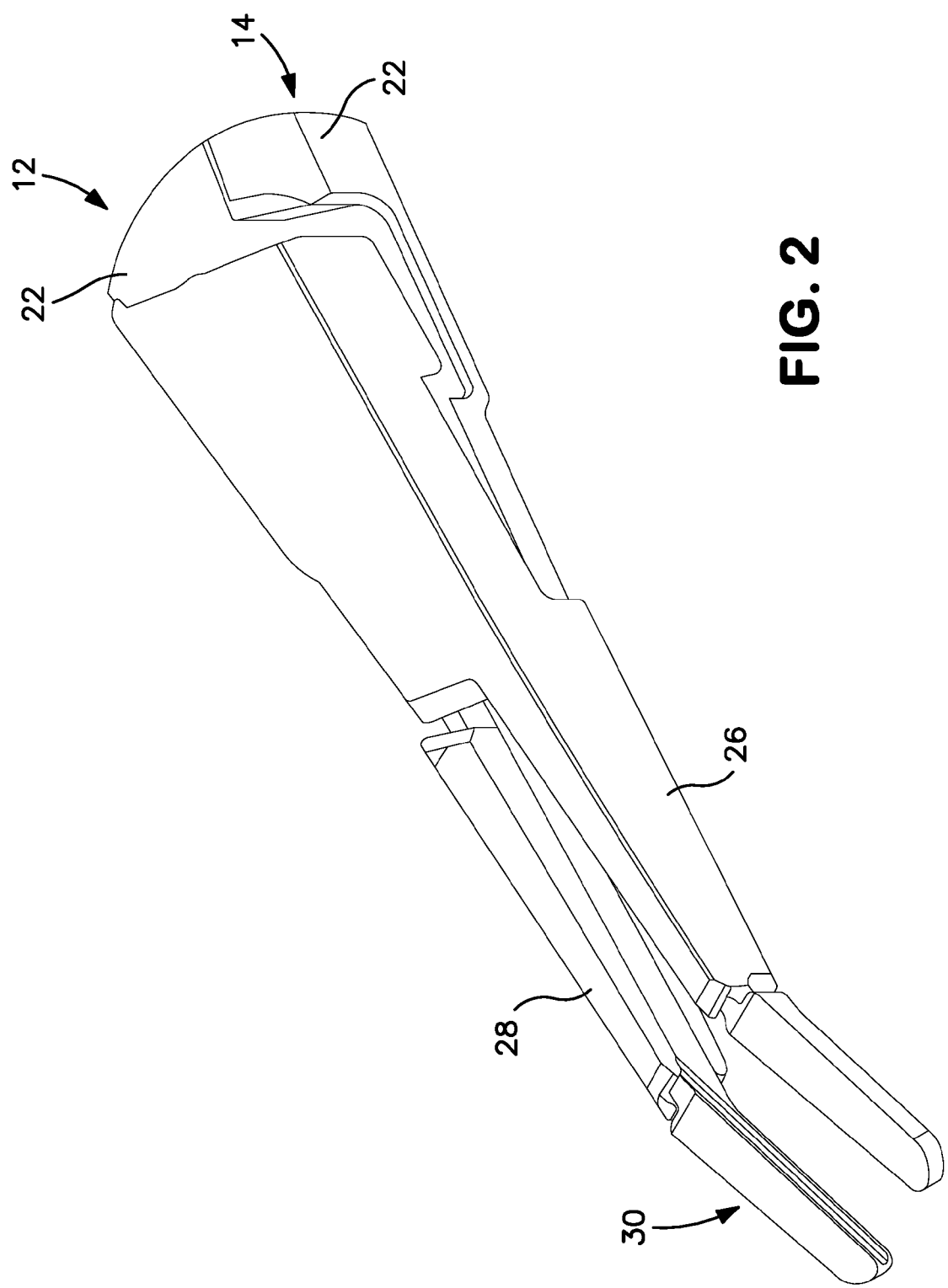
FIGS. 2 and 2A are enlarged perspective illustrations of the jaws and distal portion of the surgical clip applier in accordance with the present invention.
Figure 2A:
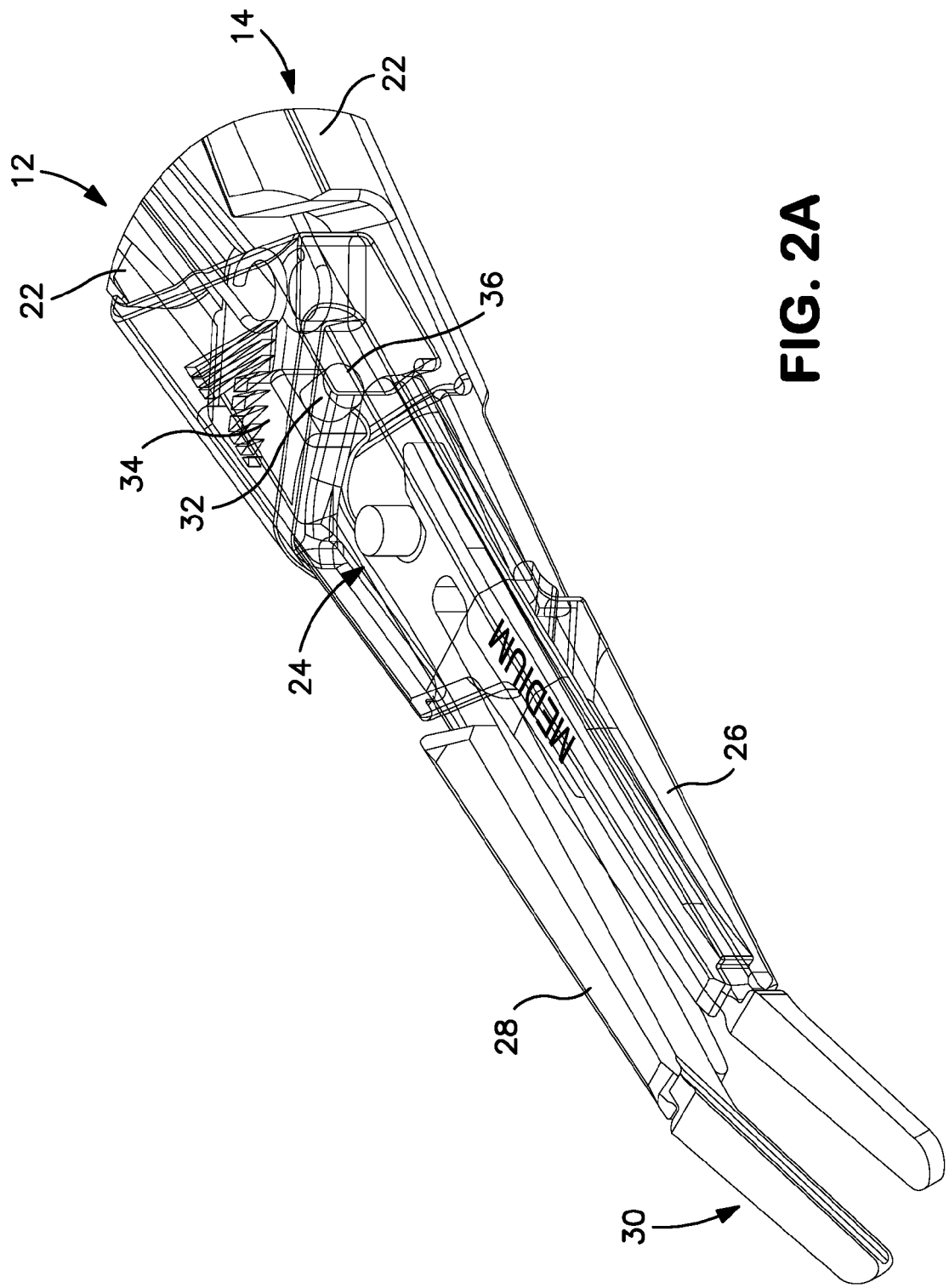

Also considering FIGS. 2 and 2A, additional detail of the jaws 30 and distal portions 26 and 28 can be seen as can a setting element 32 which, in accordance with the invention, can advantageously be used to adjust the maximum open position of the clip applier 10, preferably so that the jaws cannot accidentally open wide enough to inadvertently drop a clip before it is applied.

As shown, arms 12, 14 have portions 34, 36 which are positioned proximally of pivot point 24, and setting element 32 is a screw which is advantageously threadedly engaged in one portion 34 so that it extends toward contact with the other portion 36. Arms 12, 14 are configured such that portions 34, 36 move toward each other as arms 12, 14 are opened. This can be accomplished, for example, by having portion 34 attached to arm 14 and having portion 36 attached to arm 12. It should be readily appreciated that with such a configuration, spreading of arms 12, 14 results in closing of portions 34, 36.

FIGS. 2 and 2A also show setting screw 32 threadedly engaged in portion 34 and extending toward contact with portion 36. It should be appreciated that adjusting of setting screw 32 changes the position of setting screw 32 within portion 34 and thereby changes the relative position of arm 14 with respect to arm 12 at which setting screw 32 will contact portion 36. Thus, adjusting setting screw 32 allows fine tuning and adjusting of the maximum open position of arms 12, 14 and, therefore, jaws of clip applier 10 in accordance with the present invention.

Figure 3:
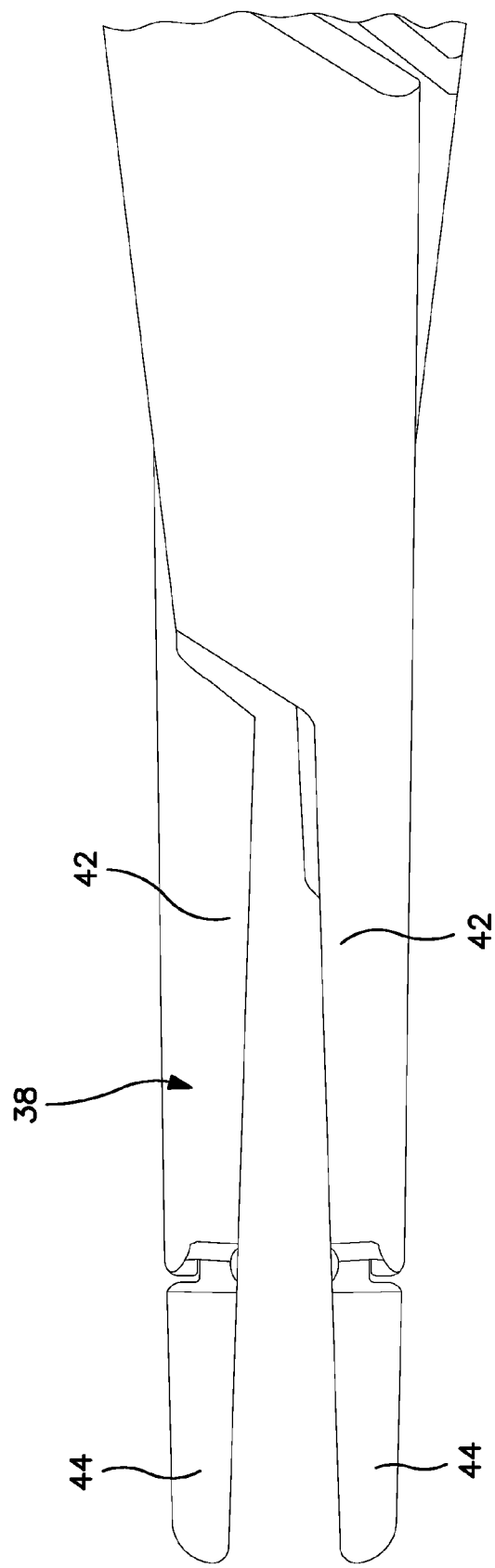
FIGS. 3 and 3A are top views similar to FIGS. 2 and 2A.
Figure 3A:
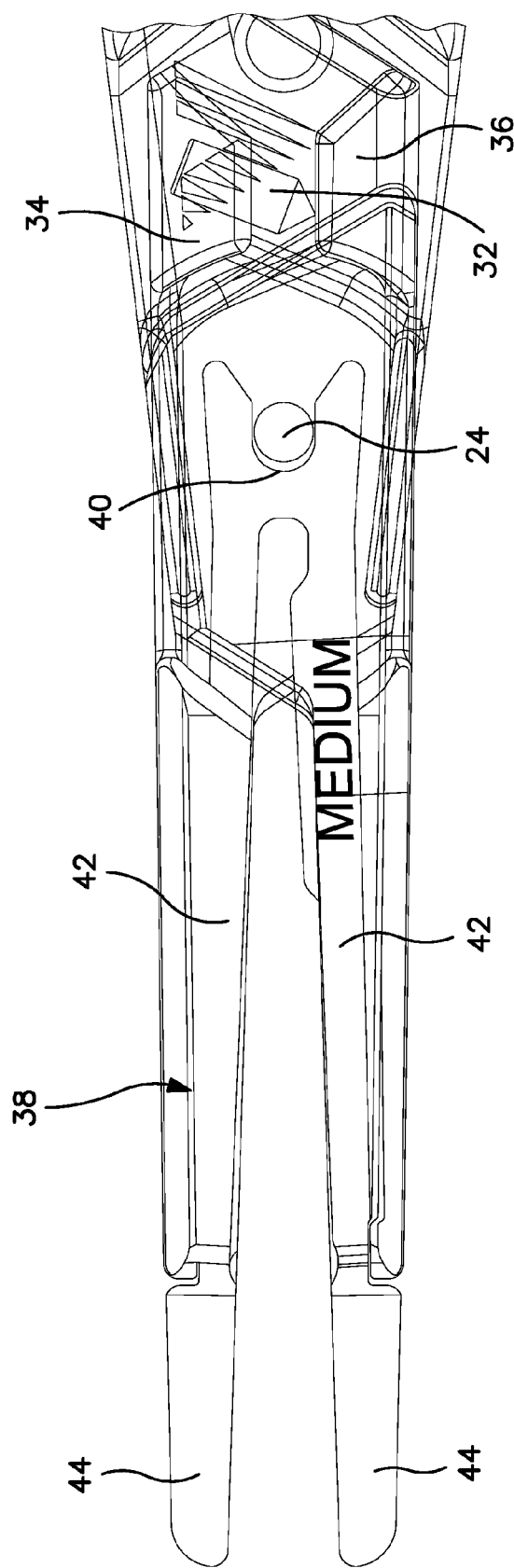

FIGS. 3 and 3A show similar details as FIGS. 2 and 2A, from a top position, and additional details of jaws 30 can also be seen which will be discussed below.

In accordance with the invention, and as discussed above, it is desirable that the jaws 30 be removable for special sterilization, etc. between uses, and eventually for being discarded and replaced with new jaws. Further, this removable nature of the jaws allows jaws of different sizes to be used with the same handle. For example, one handle could be configured to use with small, small-medium and medium jaws for applying clips of corresponding sizes.

To this end, jaws 30 can advantageously be defined by a substantially flat member 38 having a proximal end and a distal end. The proximal end can advantageously having a groove 40 for passing around or engaging pivot point 24, and two arms or prongs 42 extending distally from groove 40 to terminate in respective jaw members 44. As will further be discussed below, each prong 42 advantageously has a snap structure which releasably engages with distal portions 26, 28 so that jaws 30 can be installed into and then released from distal portions 26, 28 as desired. It should also be noted that, as best seen in FIG. 2, the actual jaw members 44 of jaws 30, which hold clips to be applied, can be angled somewhat downwardly from the plane of the prongs 42, and can also have channels defined at inwardly facing surfaces thereof, which channels serve to better hold a clip between the jaws.

In order to install jaws into a surgical clip applier in accordance with the present invention, one would follow the series of steps shown in FIGS. 4-6. FIG. 4 shows jaws 30 outside of clip applier 10, with groove 40 aligned with the distal portions 26, 28 of applier 10. Sliding the substantially flat member 38 of jaws 30 into the position shown in FIG. 5 aligns prongs 42 with ridges which extend longitudinally along distal portions 26, 28. Jaws 30 are pushed into applier 10 in this manner until the position in FIG. 6 is reached, wherein groove 40 engages pivot point 24 and a snapping structure between jaws 30 and distal portions 26, 28 engages to hold jaws 30 in place. In this position (FIG. 6), surgical clip applier 10 in accordance with the invention is ready for use.

When jaws 30 are to be removed from the clip applier, a pinching force (arrow A, FIG. 7) can be applied to jaw members 44 to disengage the snapping structure between jaws 30 and distal portions 26, 28 and jaws 30 can then distally slide out from distal portions 26, 28 as shown in FIG. 7.

FIGS. 8 and 9 show an enlarged portion of the snap assembly between jaws 30 and distal portions 26, 28. FIG. 8 shows distal portion 28 having a shoulder 46, and shows prong 42 having an oppositely directed shoulder 48. Because jaws are resilient and flexible, prongs 42 of jaws 30 will laterally compress as jaws 30 are inserted into distal portions 26, 28, until shoulder 48 snaps past shoulder 46 into the position shown in FIG. 9. In this position, shoulders 46, 48 hold jaws 30 into distal portions 26, 28 until removal of the jaws following the process shown in FIG. 7.

FIGS. 10 and 11 further illustrate an additional feature of the present invention wherein an opening spring can be included and positioned between shaft portions 22, at a position which is proximal of pivot points 24. Opening spring 50 serves to provide an additional opening force, as well as a resistive force against closing, which can be desirable depending upon the use and user of the device. As shown, opening spring 50 can have a coil portion 52 and two arms 54, 56 which can be extended into contact with shafts 22 as shown in FIG. 10.

It should be appreciated that opening spring 50 is an optional feature in accordance with the present invention since jaws 30 are ideally designed to apply a sufficient opening force to distal portions 26, 28 of arms 12, 14. Nevertheless, opening spring 50 can be incorporated into surgical clip applier 10 in accordance with the present invention, either in addition to or instead of the spring force which is otherwise generated by jaws 30 in accordance with the present invention.

Figure 12:
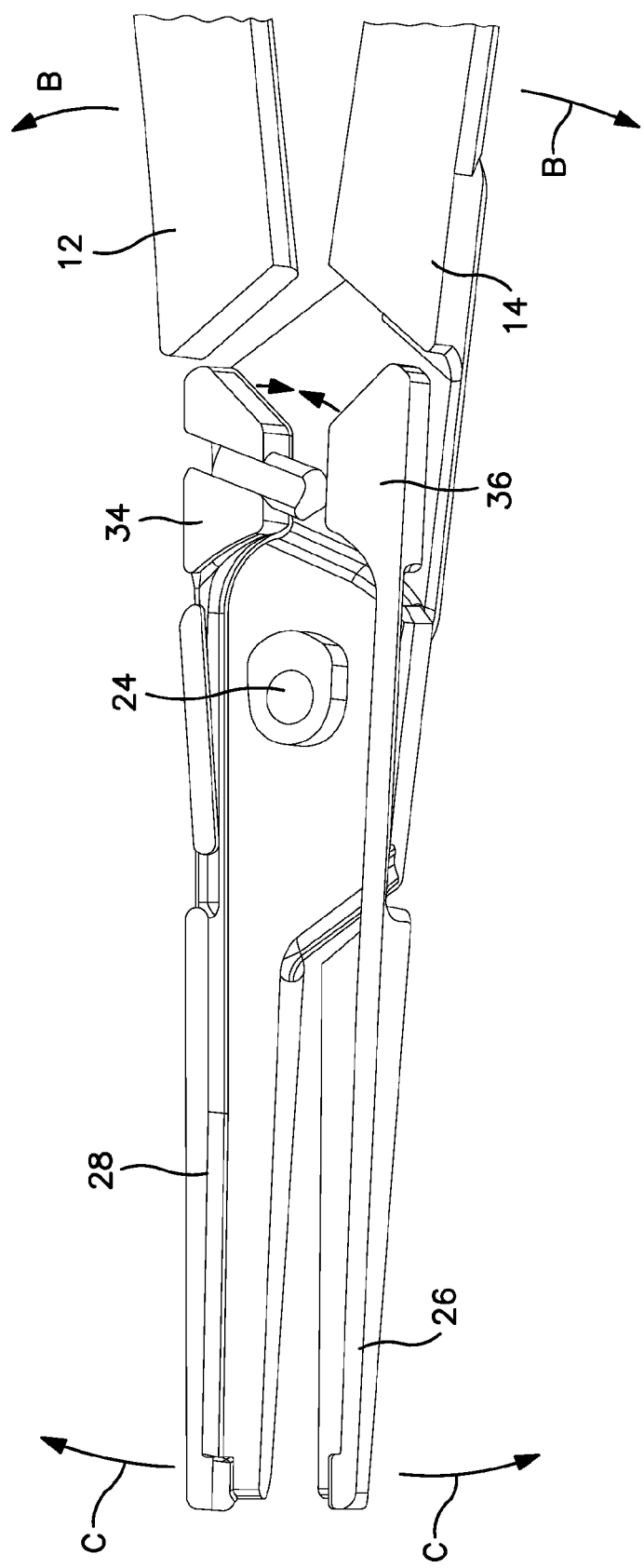
FIG. 12 further illustrates aspects of the arms of the surgical clip applier as well as the pivot connection and setting screw.

FIG. 12 further illustrates the shape and features of portions of arms 12, 14 in accordance with the present invention. Portions 34, 36 are illustrated, as is setting screw 32, and this figure also further illustrates the relationship between portions 34 and 36, setting screw 32 and operation of the device in accordance with the present invention.

When applier 10 is to be opened, arms 12, 14 are opened as shown by arrows B in FIG. 12. It should be appreciated that this motion, translated to distal portions 26, 28 around pivot point 24 would also result in an opening of distal portions 26, 28 and jaws 30 positioned therebetween as shown by arrows C. Thus, portion 34 can be associated with arm 14 while portion 36 is associated with arm 12. In this manner, when arms 12, 14 and jaws 30 are opened as shown by arrows B, C, portions 34, 36 move toward each other. Setting screw 32 engages portion 36 to stop opening of the arms and jaws in the pre-selected desired maximum position.

FIGS. 13 and 14 illustrate a preferred embodiment of a structure for pivot point 24 in accordance with the present invention, wherein portions of the arms 12, 14 are in the form of plates 53 which can engage along rounded surfaces with grooves 55 of the other of first and second arm 12, 14. In this embodiment, no screws or rivets of any kind are needed, and the arms 12, 14 engage each other along rounded surfaces that define a point of pivot therebetween. Once the plates 53 of one arm are engaged in grooves 55 of the other arm, the arms are pivotably held together in a desired position. The contacting edges of plates 53 and grooves 55 are referred to as rounded, and this rounding is in an arc which centers on the pivot point between arms 12, 14. In this way, while plates 53 and grooves 55 are engaged, they provide for smooth and stable pivot as desired.

FIG. 15 illustrates an alternate embodiment wherein a screw 57 is used to pivotably secure arms 12, 14 relative to each other.

FIG. 16 illustrates a still further alternate embodiment of the invention wherein a tapped rivet 58 is used to define pivot point 24 between arms 12, 14 and also to manage the gap between the two arms in the z-direction. With this configuration, the box lock defined between the arms can be tightened as needed to reduce misalignment in the distal area.

FIGS. 17-22 illustrate a sequence of assembly of a surgical clip applier in accordance with the present invention. As shown in FIG. 17, the assembly procedure can be started by aligning curved surfaces of a pivot point of a first arm 12 with corresponding surfaces on a second arm 14. Once these surfaces are aligned, the arms 12, 14 can be positioned together as illustrated by arrow D in FIG. 17. This results in arms 12, 14 being in the position shown in FIG. 18. Arms 12, 14 can then be pivoted toward each other such that the structure of pivot point 24 engages, and arms 12, 14 are now held together.

Figure 23A:
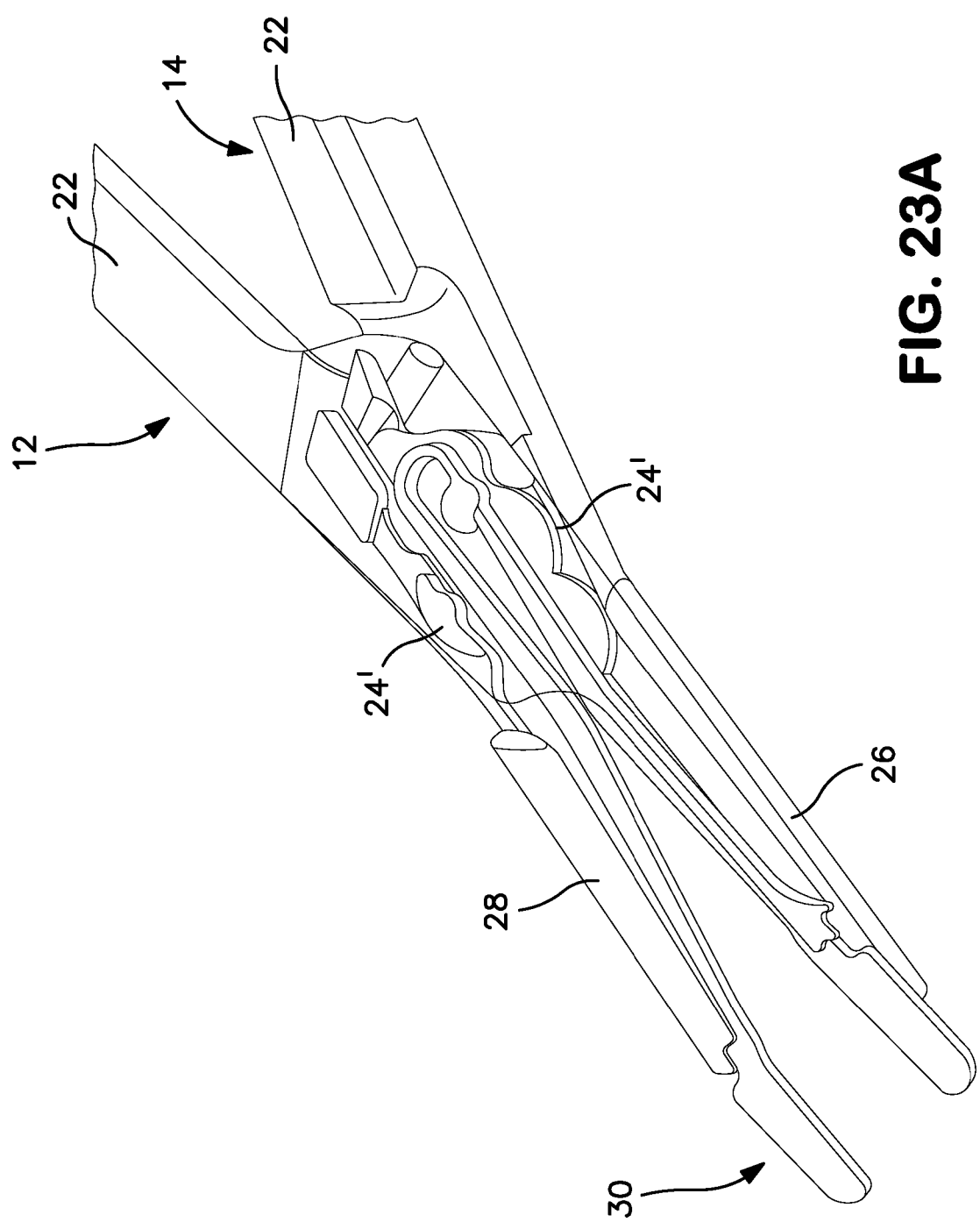

FIGS. 23 and 23A show an alternate embodiment in a similar view to that illustrated in FIGS. 2 and 2A above. In these illustrations, jaws 30 are configured differently, and have more spring force built therein. Specifically, jaws 30 have inwardly arranged surfaces 60 which are positioned along inwardly bowed flexible prongs or arms 42 such that, when the applier is closed, portions 60 engage each other and outwardly flex prongs 42. When the handles of the applier are released, the prongs or arms 42 bias the jaws back toward an open position.

In the embodiment as illustrated on FIGS. 23 and 23A, each of the prongs 42 comprise a knee defined giving the jaw a bent configuration at rest. Each knee is located between the jaw members 44 and a proximal part joining the two prongs to each other. Each knee protrudes towards the other prong. Each knee is adapted to biais a prong 42 toward its bent configuration whenever the prong is distorted into a shape different from its bent configuration. Knees may be arranged on prongs 42 so as to face each other. Each Knee may further have a curved surface facing the other knee.

When the applier is closed, the jaws are moved toward each other and at some point the knees come into contact with each other. When the applier is further closed, each bent prong is flexed by the other prong into into a more straightened configuration, and more precisely by the knee of the other prong. Thus, when the handles of the applier are released, the knees biais the straightened jaws toward their bent configuration. It should be understood that bent prongs provide a greater opening force that straight prongs such as these of the embodiment illustrated on FIGS. 4 to 6. Nonetheless, the opening spring 50 may be combined with bent jaws in order to increase the opening force even more.

Although not illustrated, only one of the jaws may be bent at rest whereas the other jaw is straight. Besides, the knees may be formed in any other biaising member than the jaws.

A further alternative as illustrated in the embodiments of FIGS. 23 and 23A is that the structure supporting the pivot point of this embodiment is not positioned inside the jaws. Referring briefly, for example, to FIGS. 3 and 3A, it can be seen that pivot point is within a portion of the jaw component. In the embodiment of FIGS. 23 and 23A, rounded internal and external surfaces are incorporated into each of the arms 12, 14 such that these surfaces 24' engage one another when the arms are engaged, for example following the procedure shown in FIGS. 17-22.

All other aspects of the embodiment of FIGS. 23 and 23 A are similar or identical to those discussed above.

The device illustrated herein has plates 53 and grooves 55 as shown in FIGS. 13-14. Once pivot point 24 is engaged in the step shown in FIG. 17 to FIG. 18, arms 12, 14 can then be pivoted toward each other around pivot point 24 until plates 53 engage in grooves 55 at which point arms 12, 14 are engaged with each other as shown in FIG. 19.

Turning now to FIG. 20, setting screw 32 can be rotated such that the maximum open position of arms 12, 14 is adjusted. Next, jaws 30 are plugged into arms 12, 14, preferably into the space between distal portions 26, 28. At this point, applier 10 is now in condition for use as shown in FIG. 22.

It should be appreciated that the present invention provides an applier for application of medical implants such as surgical clips and the like which is assembled as a scissor and which can, preferably, be permanently assembled or can be broken down into specific components as desired.

In addition, the jaw members can be made reposable so as to further enhance the efficient and effective sterile use of clip applier 10 in accordance with the present invention.

The maximum distal opening of the clip applier is readily adjustable through setting screw 32.

Loops 20 of arms 12, 14 can be provided with additional structures to render them more useful to manual operators, and this can for example include coatings and the like on the rings.

As best illustrated in FIG. 12, once jaws 30 are released, cleaning is enhanced since water can enter and escape from surgical applier 10 via many areas, providing a good flushing flow. Further, there are no dead-ends in this new structure, which further helps to reduce any amount of dust which can adhere to the inside of the device.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

The invention claimed is:

1. A surgical clip applier, comprising:
    a first arm and a second arm held together and pivotable relative to each other around a pivot point and defining proximal ends for manually controlling the applier, and distal ends;
    jaws positioned between the distal ends such that pivot of the first arm relative to the second arm opens and closes the jaws;
    a setting element movably mounted in one of the first arm and the second arm and extending into contact with the other of the first arm and the second arm to define a maximum open position of the first arm relative to the second arm, and wherein a change of position of the setting element adjusts the maximum open position,
    wherein the first arm and the second arm each define portions which are proximal of the pivot point between the first arm and the second arm such that the portions move toward each other during opening of the arms, and wherein the setting element extends from the portion of the first arm toward the portion of the second arm.

2. The applier of claim 1, wherein the setting element is a setting screw threadedly mounted in one of the first arm and the second arm and extending into contact with the other of the first arm and the second arm to define a maximum open position of the first arm relative to the second arm, and wherein rotation of the setting screw changes a position of the setting screw and thereby adjusts the maximum open position.

3. The applier of claim 1, wherein the jaws are releasably held between the distal ends.

4. The applier of claim 1, wherein the jaws have a proximal groove sized to fit around a pivot between the first arm and the second arm, and a snap structure defined between the jaws and the distal ends to releasably hold the jaws between the proximal ends.

5. The applier of claim 4, wherein, when the jaws engaged with the distal ends for use of the applier, the groove engages the pivot and the snap structure is engaged.

6. The applier of claim 4, wherein the jaws are configured such that squeezing the jaws toward each other disengages the snap structure.

7. The applier of claim 1, further comprising at least one biasing member for resiliently biasing the jaws toward an open position.

8. The applier of claim 7, wherein the biasing member comprises a first prong positioned along the first arm and a second prong positioned along the second arm to apply an opening force to the first arm and the second arm, and wherein the prongs are parts of the jaws.

9. The applier of claim 8, wherein at least one of the prongs has a knee for biasing the prong toward a bent configuration whenever the prong is straightened, the knee being further arranged to come into contact with the other prong then straighten the bent prong whenever the jaws are moved towards each other.

10. The applier of claim 7, wherein the biasing member comprises an opening spring positioned relative to the first arm and the second arm to apply an opening force to the first arm and the second arm.

11. The applier of claim 1, wherein the first arm is pivotably mounted to the second arm with at least one slidable plate on one arm engaged in a groove on the other arm.

12. The applier of claim 1, wherein the first arm is pivotally mounted to the second arm with a screw assembly.

13. The applier of claim 1, wherein the first arm is pivotably mounted of the second arm with a tapped rivet.

* * * * *